(12) United States Patent
Popescu (10) Patent No.: US 10,580,212 B2
(45) Date of Patent: Mar. 3, 2020

(54) METHOD AND REPRESENTATION SYSTEM FOR THE MULTISENSORY REPRESENTATION OF AN OBJECT

(71) Applicant: Siemens Healthcare GmbH, Erlangen (DE)

(72) Inventor: Stefan Popescu, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 149 days.

(21) Appl. No.: 15/485,567

(22) Filed: Apr. 12, 2017

(65) Prior Publication Data

US 2017/0294050 A1 Oct. 12, 2017

(30) Foreign Application Priority Data

Apr. 12, 2016 (EP) .................................... 16164861

(51) Int. Cl.
| | |
|---|---|
| *G06T 19/00* | (2011.01) |
| *B33Y 10/00* | (2015.01) |
| *B33Y 30/00* | (2015.01) |
| *B33Y 50/02* | (2015.01) |
| *G05B 13/04* | (2006.01) |
| *G05B 19/4099* | (2006.01) |
| *G06F 19/00* | (2018.01) |

(52) U.S. Cl.
CPC .......... *G06T 19/006* (2013.01); *B33Y 10/00* (2014.12); *B33Y 30/00* (2014.12); *B33Y 50/02* (2014.12); *G05B 13/04* (2013.01); *G05B 19/4099* (2013.01); *G06F 19/321* (2013.01); *G05B 2219/49023* (2013.01)

(58) Field of Classification Search
CPC ....... G06T 19/006; G06T 17/00; G06F 19/00; G06F 19/321; G05B 13/04; G05B 19/4099; G05B 2219/49023; B29C 64/386; B33Y 30/00; B33Y 10/00; B33Y 50/02; G02B 27/2278; G02B 26/10
See application file for complete search history.

(56) References Cited

U.S. PATENT DOCUMENTS

| | | | |
|---|---|---|---|
| D740,811 S | 10/2015 | Bosveld et al. | |
| 9,275,451 B2 * | 3/2016 | Ben-Haim | ............ G06F 19/321 |
| 10,056,012 B2 * | 8/2018 | Geri | ....................... G09B 23/28 |

(Continued)

OTHER PUBLICATIONS

Mendez et al., Interactive context-driven visualization tools for augmented reality, Proceedings of the 5th IEEE and ACM International Symposium on Mixed and Augmented Reality, p. 209-218, Oct. 22-25, 2006. (Year: 2006).*

(Continued)

*Primary Examiner* — Maurice L. McDowell, Jr.
*Assistant Examiner* — Donna J. Ricks
(74) *Attorney, Agent, or Firm* — Schiff Hardin LLP (57) ABSTRACT

In a method and system for the multisensory representation of an object, multidimensional digital model data of the object are provided to a processor. An actual three-dimensional object model is produced on the basis of at least part of the multidimensional digital model data of the object. The position of the object is recorded subsequently. At least part of the multidimensional digital model data of the object is displayed by an AR display device depending on the position of the object model.

14 Claims, 4 Drawing Sheets

(56) References Cited

U.S. PATENT DOCUMENTS

| | | | | |
|---|---|---|---|---|
| 10,405,925 | B2* | 9/2019 | Jaquet | G16H 50/50 |
| 2002/0046368 | A1* | 4/2002 | Friedrich | G05B 19/409 |
| | | | | 714/45 |
| 2012/0212509 | A1* | 8/2012 | Benko | G03B 35/00 |
| | | | | 345/633 |
| 2013/0162673 | A1 | 6/2013 | Bohn | |
| 2013/0293939 | A1 | 11/2013 | Rotschild et al. | |
| 2014/0015833 | A1 | 1/2014 | Kang et al. | |
| 2014/0210947 | A1* | 7/2014 | Finn | G01C 15/002 |
| | | | | 348/46 |
| 2015/0250934 | A1* | 9/2015 | Min | A61M 1/1053 |
| | | | | 623/3.11 |
| 2016/0066862 | A1* | 3/2016 | Taylor | A61B 5/7275 |
| | | | | 600/485 |
| 2017/0228139 | A1* | 8/2017 | Goslin | G06F 3/04845 |

OTHER PUBLICATIONS

Mendez et al., "Interaction Context-Driven Visualization Tools for Augmented Reality," IEEE/ACM International Symposium on Mixed and Augmented Reality, 2006, pp. 209-218 (2006).
Bartlett, "The Use of Augmented Reality in the Operating Room: a Review," www.cs.ubc.ca/~tmm/courses/533-09/projects/john/report.pdf (2016).
European Action dated Nov. 11, 2019, for Application No. 16 164 8613.
Anonymous: Inition develops "augmented 3D printing" for architects, Jan. 4, 2013—Internet URL:https://web. archive.org/web/20160331150305/https://www.dezeen.com/2013/01 /04/inition-develops-augmented-3d-printing-forarchitects/.

* cited by examiner

METHOD AND REPRESENTATION SYSTEM FOR THE MULTISENSORY REPRESENTATION OF AN OBJECT

BACKGROUND OF THE INVENTION

Field of the Invention

The present invention concerns a method for the multisensory representation of an object, and a representation system suitable for this purpose.

Description of the Prior Art

The representation and simultaneous perception of reality and its physical properties in an interactive, completely or partially virtual environment, which is computer-generated in real time, is described as virtual reality (VR) or augmented reality (AR). Usually, it is primarily the visual component of reality that is replaced. In the case of augmented reality, for example, virtual objects or additional virtual information are superimposed on the actual environment. A user can interact with the represented virtual elements, for example, rotating them or zooming in on them or zooming out from them. For this purpose, the user usually wears a pair of AR glasses as described, for example, in US 2013/0162673. The virtual objects represented therefore may have a level of detail and information exceeding reality, but are inherently intangible.

Moreover, 3D printers are known. Objects with almost any structure can be produced with these printers. In principle, a multiplicity of materials can be used for this purpose. However, the number of materials actually used to produce an object is restricted to a few, due to the nature of the 3D printer or for financial reasons. At present, it is therefore difficult, or at least uneconomic, to produce a model of an actual object with the use of a 3D printer, such as with natural coloring. Feasible models are, by their nature, static and usually opaque. Dynamic, variable coloring and a visible representation of integrated details are therefore difficult or currently impossible with the resources of an individually producible actual model.

SUMMARY OF THE INVENTION

An object of the invention is to provide a method for the representation of an object and a representation system for this purpose, wherein an optic and haptic perception of the object is enabled.

The inventive method for the multisensory representation of an object includes the following steps.

Firstly, multidimensional digital model data of the object are provided to a processor. Then an actual three-dimensional object model based on at least part of the multidimensional digital model data of the object is produced under control of the processor. In a subsequent step, a position of the actual three-dimensional object model is detected and a signal representing the detected position is provided to the processor. Finally, at least part of the multidimensional digital model data of the object is displayed, depending on the position of the object model, at an "AR display device". An AR display device is understood to mean an apparatus that is designed to reproduce or display AR content (augmented reality content).

The method according to the invention therefore provides a multisensory representation, i.e. an output of the object perceptible with several senses (visual, haptic). The object to be represented may be any object. Preferably, however, it is an object that is difficult to access, with which it is possible to interact largely freely in the context of the method.

Multidimensional digital model data are also referred to as model data for short below, and constitute a digital model of the object (digital object model). The model data enable a numerical description of the object, for example, through the file of space coordinates of a point cluster representing the object. Therefore, the digital model may be a pixel raster, i.e. a three-dimensional pixel graphic, or a vector model of the object, wherein a transition from discrete points to scalable lines and surfaces can also take place using suitable algorithms.

Multidimensional digital model data accordingly include structural data that describe the shape and arrangement of individual elements of the object. Such data embody, for example, at least the surface of the object. Preferably, color data and data relating to other properties of the object are also spatially associated with the structural data.

The model data can be suitably stored before starting the method, or can be modeled directly for the method, for example, by CAD software (computer-aided design). The model data can also be based on three-dimensional image data of the object recorded, for example, with a 3D camera (stereo camera, TOF camera, etc.). "Based on" means that the corresponding data, for example, the image data and/or the CAD data, include the actual model data or other data derived from the model data such as modified structural data and the like. The multidimensional digital model data therefore constitute a uniform overall model that, for example, also includes design data, functional data, dynamic data, modified structural data and the like.

It is also possible for only part of the model data, e.g. in the form of a basic model, to already be stored before the method, and another part of the model data to be generated for the method, for adjustment of the basic model.

Based on at least part of the three-dimensional model data of the object, i.e. particularly when using the digital model, an actual three-dimensional object model is produced. The part of the three-dimensional model data that is used preferably is the structural data of the object. In production, therefore, the haptic or structural properties of the object and the external shape are reproduced in as realistic a manner as possible.

The actual object model produced can now be felt, rotated and positioned at will by an operator. In the process, its location, i.e. its position and orientation, are recorded using suitable detectors, for example, sensors or cameras. For example, image data of the actual three-dimensional object model can be generated and then compared to the digital model and recorded thereon.

For example, with the use of this comparison, display takes place depending on the position of the object model. Part of the model data is displayed virtually on the object model, wherein this data preferably supplement or augment the actual object model. In this way, for example, the color data also included in the model data can be displayed on the actual object model. The display can be transparent so that, for example, the actual shadows of the object model are perceptible, but the object model can also be superimposed opaquely so that the corresponding image area is selectively cut out and completely covered by the virtual representation. The display is preferably three-dimensional, i.e. so that three-dimensional image data generated from the model data are displayed in the correct perspective on the actual object model.

A system of projectors can be used as the AR display device, for example, wherein the projectors each project the three-dimensional image data onto the object model from different directions. Alternatively, the AR display device can be designed in the form of typical AR glasses or an AR headset. Unlike the display by projector, the display then is only for an operator and also only from the operator's perspective. Both the three-dimensional object model and the superimposed virtual display are therefore based indirectly or directly on the same model data or on the same digital model. The virtual display not only augments the actual object model to as realistic a representation as possible, but also offers the opportunity to also display information in addition to the actual object model, and thus enables a reality-enhancing representation.

The aforementioned representation system for an object is designed such that it performs the steps of a method according to the invention for the representation of an object. For this purpose, it has at least one storage device, a manufacturing apparatus, an object sensing unit and an AR display device.

The basic components, particularly the display-calculation unit of the representation system according to the invention, can largely be designed in the form of software components, but these components can also be partly realized, especially if particularly rapid calculations are involved, in the form of software-supported hardware, for example, FPGAs or the like. Likewise, the necessary interfaces can be designed as software interfaces, for example, when only the transfer of data from other software components is involved. However, they can also be designed as hardware-based interfaces, which are controlled by suitable software.

Largely software-based implementation has the advantage that components already in use can continue to be used, modularly and simply upgraded by a software update to operate in the manner according to the invention. Thus, the above object is also achieved by a non-transitory, computer-readable data storage medium encoded with a program code. The storage medium can be loaded directly into a memory of a processor of a presentation apparatus of a representation system. The program code cause all the steps of the method according to the invention to be implemented when the program code is executed in the presentation apparatus. The program code can be embodied in a computer program product that may also have additional components such as documentation and/or additional components including hardware components such as, for example, hardware keys (dongles, etc.) for use of the code.

The non-transitory, computer-readable storage medium can be, for example, a memory stick, a hard disk or another transportable or integrated data carrier.

Individual features of various exemplary embodiments or variants can be combined to form new exemplary embodiments or variants.

The method according to the invention therefore provides the opportunity to clearly present an object and to make even complex relationships involving the object easier to understand by the information presented in augmented reality. For this purpose, it is not necessary that the object to be presented is accessible or exists in reality at all. It must only be possible to provide model data of the object. The method is therefore particularly suitable for the representation of objects which are found inside a body, wherein the multidimensional digital model data is preferably based on image data of the object that is compiled with the use of a medical imaging method, which can obtain data from inside a body.

The body generally refers to a larger whole containing the object, but preferably is the body of a patient. Accordingly, the object preferably represents an internal organ of the patient. The imaging method correspondingly supplies image data from inside the body, i.e. it forms internal structures of the body as a three-dimensional volume data set. Examples of such an imaging method are computed tomography (CT), magnetic resonance tomography (MRT), ultrasound and positron emission tomography (PET). The image data set can also be generated using a combination of these methods.

It is possible to present the object inside the body, in other words, preferably an internal organ of a patient, palpably and clearly without injuring the body. The combination of tangible object model and virtual display makes it possible, for example, for a surgeon to interact with as realistic a representation of the organ concerned as possible before an invasive procedure, and thus plan the intervention.

The multidimensional digital model data are preferably based on three-dimensional image data of the object that have been generated by software, particularly preferably by a CAD program. As noted, no object actually in existence is therefore required for the method according to the invention, as virtually created image data that represent the object with the required level of detail suffice.

Particularly preferably, the multidimensional digital model data also includes image data from inside the object itself. Such data can be taken into consideration during production of the actual object model so that the actual object model not only has the most accurate structure possible superficially, but also internally. Moreover, with virtual display the data permit the viewer's gaze to penetrate to a certain depth below the surface of the object model. Unlike a purely superficial representation, structures lying beneath the surface thus can also be displayed and/or considered, for example, to plan an operation.

The multidimensional digital model data can include functional and/or dynamic data. Dynamic data changes in a chronological sequence, such as in a fixed sequence, or if applicable, depending on interactions. Functional data represent functions and/or properties of the object. Both functional and dynamic data are generally not readily visible on the actual object. Such data therefore represent a virtual augmentation of actual perception during display. For example, fluid or gas flows can be visualized as vector displays and/or as a spatial temperature distribution, and their chronological sequence can be shown in false color in the context of display on the actual object model.

Preferably, the functional and/or dynamic data are based on the imaging method. Thus, for example, a patient's brain waves can be recorded by functional MRI using BOLD (blood oxygen level dependent) contrast and if necessary, also displayed in a chronological sequence on an actual object model of the patient's brain. In this manner, for example, blood flows in a patient's vessels and/or heart can also be represented as a virtual display on a corresponding actual object model.

Preferably, the functional and/or dynamic data are based on a simulation. For example, a virtual model is created for a variable or property of the object for display by suitable software. For example, in a simulation in accordance with the known Finite Element Method (FEM), an object is known to be divided into individual elements and a differential equation or a differential equation system numerically thus achieved under defined framework conditions. Using this method, spatial and if necessary, chronological sequences of variables such as temperature, material stress or the like, can be determined, taking into account the structure of the object and external framework conditions. Further examples of simulation methods are BEM (Boundary Element Method), FDTD (Finite Difference Time Domain) and the like. The determined variables can then be displayed as display data spatially correlated to the object, such as by false-color representation. A viewer can therefore record the information concerning the variable directly on the object.

Preferably, the status of the actual three-dimensional object model is therefore also recorded and the multidimensional digital model data of the three-dimensional object are displayed in additional dependence on the status of the actual three-dimensional object model. A status of the actual object model describes a particular property such as the current temperature. It is also possible to record whether the actual object model is deformed, i.e. for example, twisted, as a status. The status of the object model can therefore in particular also have some influence on the aforementioned FEM simulation as an external framework condition. Furthermore, it is possible to record as a status of the actual object model whether the object model is still complete or whether, for example, parts of the object model have been removed by a viewer. The multidimensional digital model data are therefore generally adjusted to the actual status of the actual object model.

Preferably, the position and if necessary, also the status of the actual three-dimensional object model, are recorded on the basis of markers. These can be arranged as optical markings on the object model and/or in the form of anatomical landmarks. Further examples of markers are RFID chips (Radio Frequency Identification), which can be introduced into the object model, LEDs and/or resources for non-optical tracking methods, such as magnetic tracking or acoustic tracking.

The AR display device preferably has a number of projectors. Projectors are understood to mean projectors which project an image transmitted in the form of image data onto a surface as a photograph. The projectors are arranged with directions of projection defined in relation to each other for this purpose. As a result, AR display takes place preferably from all sides on the actual object model. This enables not only a viewer but all the people in the room to perceive the AR display on the actual object model without the need for a separate AR display device for each viewer.

Preferably, the actual three-dimensional object model is produced with the use of a 3D printer and/or a CNC machine. Like the 3D printer, the CNC machine is also computer-supported and numerically controlled (Computerized Numerical Control). As noted, both these manufacturing apparatuses provide the opportunity for the relatively simple and inexpensive production of an actual three-dimensional object model on the basis of a digital model, for example, on the basis of the present multidimensional digital model data. In particular, complex shapes that are difficult or impossible to produce using other existing machines can be advantageously produced by the 3D printer. The aforementioned intrinsic disadvantage, that a realistic representation of color is not easy to achieve cost-effectively in this way, is overcome according to the invention by the virtual display of color data included in the model data.

Preferably, it is ensured that haptic properties of the actual three-dimensional object model essentially correspond to haptic properties of the object. This means that features of the object to be palpated such as, for example, the surface structure, rigidity and the like, are reproduced as realistically as possible when producing the object model. Thus, for example, in a corresponding 3D printing method the rigidity is determined by the extent of networking of polymers used. The extent of networking of the polymers is, for example, controlled photoreactively by the intensity of incident light.

The actual object model produced in this way can be perceived not only as realistically as possible haptically and visually using the method according to the invention, but also display additional information for the viewer in augmented reality by the AR display.

DESCRIPTION OF THE PREFERRED EMBODIMENTS

Figure 1:
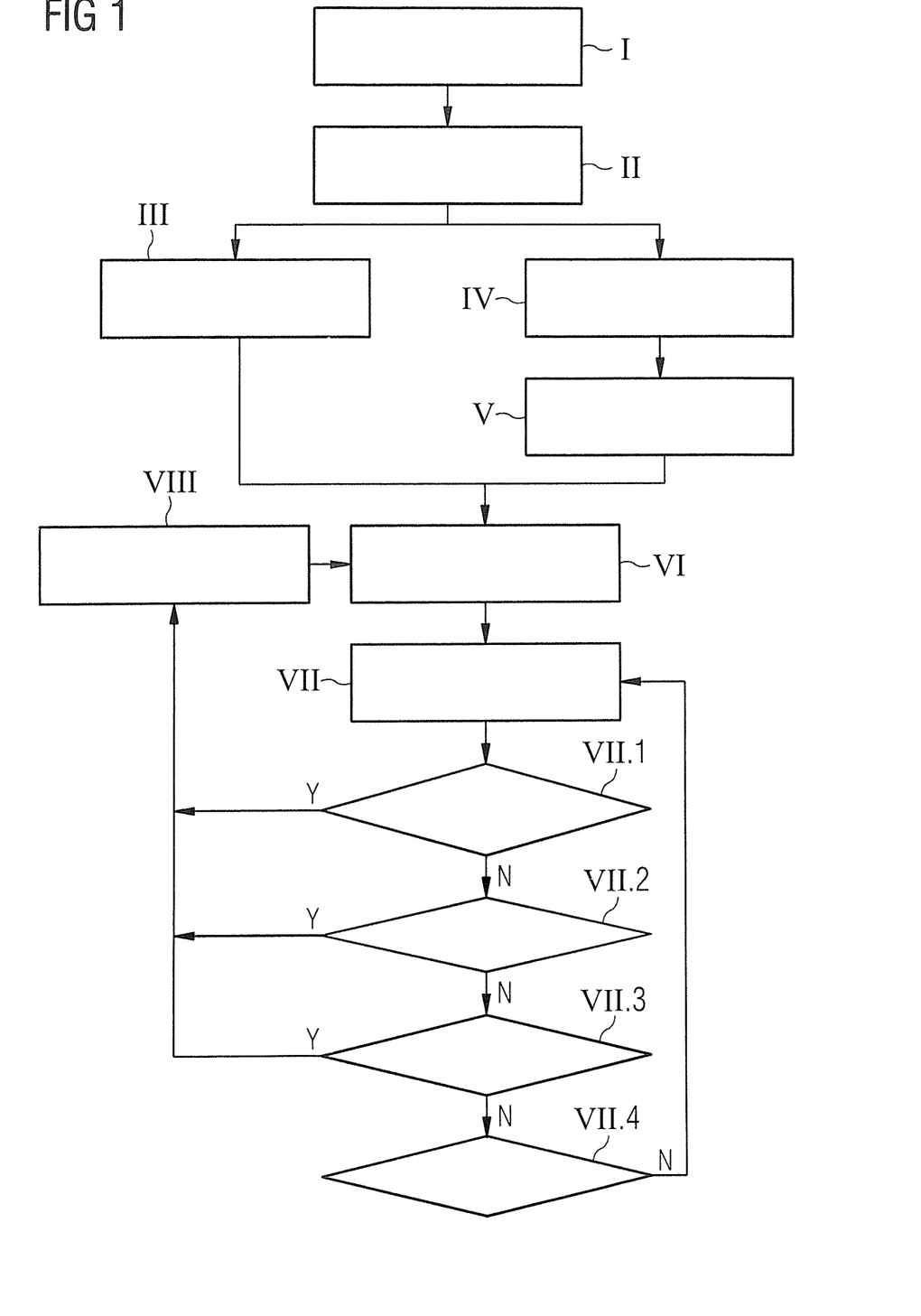
FIG. 1 is a flowchart of an exemplary embodiment of a method according to the invention for the multisensory representation of an object.

FIG. 1 shows a flowchart of a method according to the invention in eight steps, as an example. With regard to the apparatus-specific reference characters, reference is made to FIG. 2 which is subsequently described in more detail. In a first step I, image data BD of a heart O in a body K of a patient is recorded as object O by an MRI scanner 2. The image data BD includes both structural data and dynamic variable data of the heart, as well as flow data of blood flowing through the heart. In addition, physiological data that can be visualized, such as an ECG signal, are recorded.

Based on these data and taking into account further stored data, such as color data as a general color scheme for the heart, in a second step II an individual uniform digital model of the heart O and its dynamic properties is created. The digital model can be created, as in this case, on the basis of measurements. Alternatively, it can be additionally or solely based on a virtual model created by CAD software. The digital model is voxel-based in this example, wherein each voxel (volume pixel) is assigned a Cartesian coordinate (x, y, z) and linked to the data spatially assigned thereto. The digital model is maintained in a memory 12 in the form of multidimensional digital model data D.

In a third step III, an AR-compatible representation of the heart O and its properties is generated on the basis of the multidimensional digital model data D. In a fourth step IV, construction data KD are generated by a 3D printer 3 from the multidimensional digital model data D of the heart O in a file format (STP, VRML, 3MF, CNC), which is suitable for producing an actual model of the heart M as an actual object model of the heart O. In the subsequent fifth step V, the model of the heart M is created with the 3D printer. Step III can be performed in parallel with steps IV and V.

The model of the heart M produced in this way can now be examined and manipulated by a viewer B in a sixth step VI. The viewer B can rotate, position, preferably also deform, for example, twist, press in, etc. the model of the heart M as required, and actually perform an invasive intervention thereon. In parallel, additional so-called AR elements based on the multidimensional digital model data D, which represent the actual model of the heart M in augmented reality, are superimposed by an AR headset 30 as an AR display apparatus 30. Depending on predefined or currently defined settings or at the discretion of the viewer B, these elements can be displayed with an adjustable degree of transparency, namely partially or completely superimposed over the model of the heart M. The model of the heart M therefore can be optically perceived completely virtually so that essentially it is only actually detected by the sense of touch.

Depending on the setting or at the discretion of the viewer B, all parts of the multidimensional digital model data D provided can also be displayed as AR elements in combination, if necessary. Thus, for example, realistic colors can be displayed on surfaces of the model of the heart M at the same time as having a certain transparency, while anticipated blood flow rates in ventricles of the heart and vessels are visualized. In particular, it is also possible to hide actual areas of the model of the heart M virtually, in other words, to present a virtual incision in the model of the heart M. Chronological developments of other variables such as temperatures and/or fluid flows can also be presented like a film to augment the model of the heart M. The display is automatically updated at discrete intervals (frames) for this purpose, although these are perceived as a continuous image sequence by the viewer B.

As aforementioned, the viewer B influences a position and if necessary, also a status of the model of the heart M and in doing so, also alters a position of the model of the heart M or their own perspective. These changes relevant to the display are recorded in the seventh step VII. The AR headset has a video camera 31, 32 for this purpose, which records image data in the form of visual data VD of the model of the heart M. The model of the heart M also has markers for this purpose which are already taken into account in step IV and produced or employed in step V.

For the detection of changes in the position or status of the model of the heart M, the seventh step VII has four sub-steps VII.1, VII.2, VII.3, VII.4. In the first sub-step VII.1, the change of position, in other words, a deviation from the previous position and orientation with regard to a spatial reference system, is examined. If the result is negative N, in other words, if no change is detected, the second sub-step VII.2 is commenced, in which the change of perspective of the viewer B is examined. To record the perspective of the viewer, the AR headset 30 has resources, for example, markers, to record the gaze of the viewer B in the spatial reference system. If the result is negative N, in other words, if no change is detected here either, the third sub-step VII.3 is commenced, examining whether a new frame of the AR elements presented like a film should be displayed. If the result is negative N, in other words, if no update is necessary, the method continues with sub-step VII.4, which is described below.

If the result of one of the steps VII.1 to VII.3 is positive Y, in other words, if a corresponding change has been recorded, the method is continued in the eighth step VIII. Other sub-steps will therefore not be taken in this case but the corresponding changes for an update of the display recorded. In the eighth step VIII, the AR elements to be displayed are calculated and rendered anew accordingly based on the recorded changes. The updated AR elements are displayed in a rerun of the sixth step VI, in which the viewer B can undertake further manipulations of the model of the heart M.

The final fourth sub-step VII.4 examines whether the method for representation should be terminated. This decision can be made, for example, as a result of an entry by the viewer. If the result is negative N, sub-steps VII.1 to VII.4 are repeated until the AR elements in the eighth step VIII are re-rendered. If the result is positive, the method is terminated.

Figure 2:
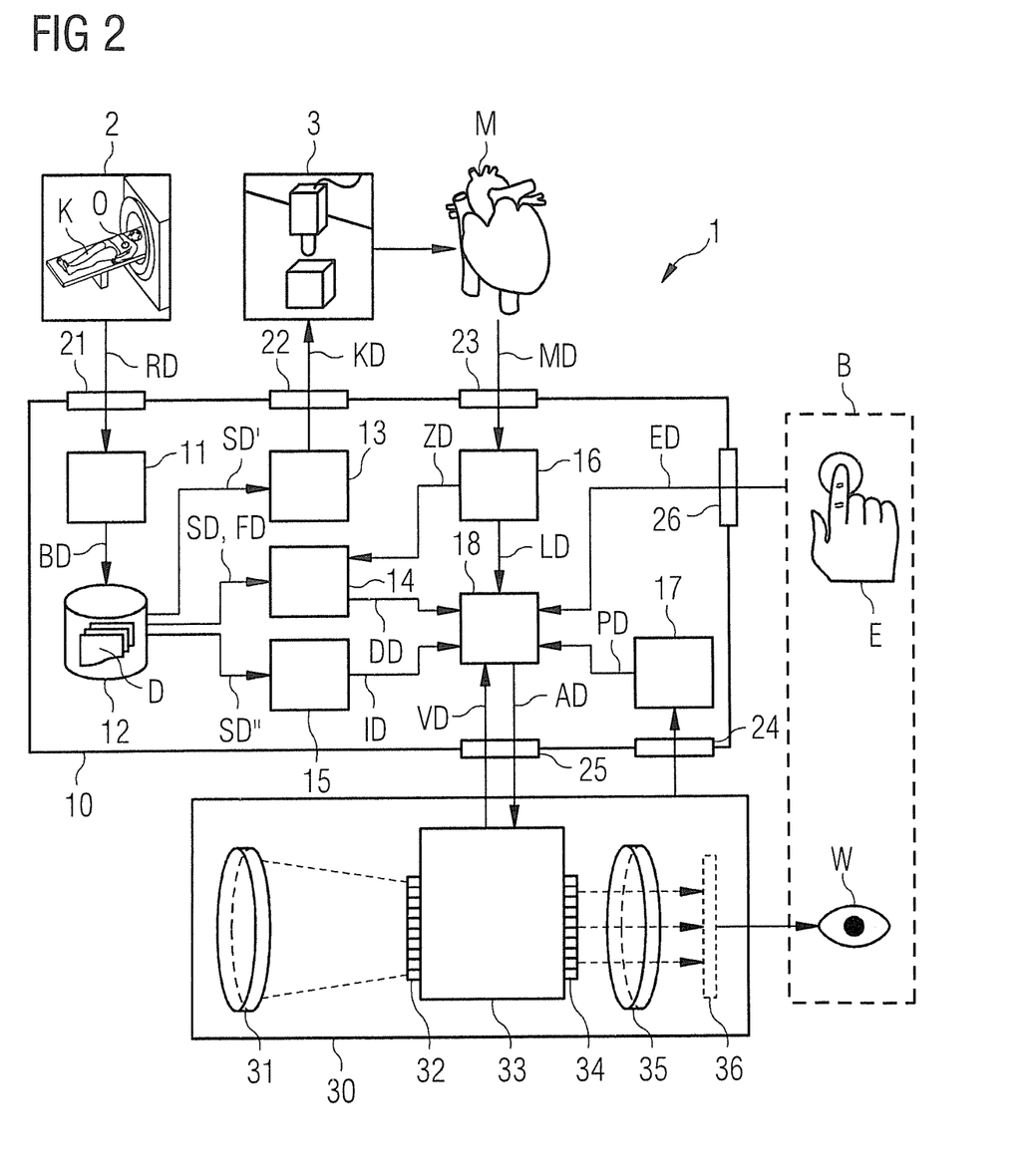
FIG. 2 is a block diagram of an exemplary embodiment of a representation system according to the invention.

As an example, FIG. 2 shows a block diagram of a representation system 1 according to the invention with which a viewer B, likewise shown diagrammatically, interacts. The representation system 1 has a central presentation apparatus 10 and, as peripheral components, an MRI scanner 2 as a medical imaging modality, a 3D printer 3 as a computer-controlled manufacturing apparatus 3, and an AR headset 30 as an AR display device.

The MRI scanner 2 acquires raw data RD from a body K of a patient and in particular, from their heart O as object O. The raw data RD are transmitted via a raw data interface 21 to a reconstruction computer 11 of the presentation apparatus 10. The reconstruction computer 11 reconstructs image data BD from the raw data RD and stores it in the memory 12. Frequently the reconstruction device 11 is also assigned to the MRI scanner 2 so that the presentation apparatus 10 receives direct image data BD via a suitable interface. Further data such as color schemes and/or an adaptable basic model for the object O, which are added to the image data BD, are preferably kept in the memory 12. Overall, a uniform digital model of the heart O as the object for presentation is thus produced from the image data BD. The digital model is stored in the memory 12 in the form of multidimensional digital model data D. Of the multidimensional digital model data D, functional data FD and structural data SD, SD', SD" of the heart O are included, which reproduce the spatial arrangement of individual tissue components in relation to each other as well as their detailed internal structure and properties.

A set of structural data SD' modified for the production of an object model M is transmitted to a construction specification processor 13. The modified structural data SD' contain additional information regarding markers, which are also to be produced during subsequent production. The construction specification processor 13 converts the structural data SD' into construction data KD with a suitable format for a 3D printer 3. The construction data KD are transmitted to the 3D printer via a production interface 22. In accordance with the construction data KD, the 3D printer creates an actual 3D model of the heart, which is referred to as a model of the heart M hereinafter.

The model of the heart M is a realistic reproduction of the heart O of the patient in terms of shape and structure (except for additional markers, if applicable). Accordingly, it can be viewed and manipulated at will by the viewer B on the basis of procedural step VI described in FIG. 1. During manipulation, the position and orientation of the model of the heart M are recorded as model data MD using suitable sensors. In the case of optical markers, cameras, for example, the subsequently described CCD sensors 32 with the lens 31 of the AR headset 30 are used for recording, in the case of RFID chips, corresponding reading devices, etc. The recorded model data MD are transmitted via a model acquisition interface 23 to a model acquisition processor 16. This evaluates the model data MD in the context of a spatial reference system, and from that evaluation determines position data LD regarding the position and orientation of the model of the heart M. In addition, for example, status data ZD relating to properties such as temperature, deformation, etc. of the model of the heart M are recorded by temperature sensors and/or other suitable sensors.

From the memory 12, modified structural data SD" for the display of invariant data ID are transmitted to a structure specification processor 15. In addition to structural information, the modified structural data SD" include further data that does not change with manipulation over time such as, for example, a color scheme for the model of the heart M.

The structural specification processor 15 converts the modified structural data SD" to invariant data ID, which has a format suitable for AR display, and transmits the invariant data ID to a display calculation processor 18.

The memory 12 also transmits the structural data SD and the functional data FD to a dynamic specification processor 14. This combines the structural data SD and the functional data and, using the status data ZD, calculates dynamic data DD in a format suitable for AR display and transmits the dynamic data DD to a display calculation processor 18. The dynamic data DD permit, for example, an AR display of the current temperature, material stress under deformation and flow representations, etc.

Furthermore, the position and the orientation of the AR headset 30 are recorded. This recording can take place using the same sensors as for the recording of model data MD. These also forward the corresponding data to a perspective recording unit 17 via an AR recording interface 24. Likewise using the spatial reference system, it determines the perspective of the viewer B and forwards corresponding perspective data PD to the display calculation processor 18.

The display calculation processor 18 also receives visual data VD from the AR headset 30 from the perspective of the viewer by way of an AR image interface 25 and manual entries E of the viewer B by way of an input interface 26. Using the visual data VD, the invariant data ID, the dynamic data DD, the position data LD and the perspective data PD, the display calculation unit 18 calculates display data AD in accordance with predefined settings or the manual entry E of the viewer B. The display data AD therefore reflects a view from the perspective of the viewer B of the model of the heart M to which virtual AR elements have been added by the presentation apparatus 10. The display data AD is transmitted to the AR headset 30 via the AR image interface 25.

The AR headset 30 has a display interface 33 for receipt of the display data AD and for transmission of the visual data VD. The visual data VD are recorded by a camera arrangement. The camera arrangement has a lens 31 as an optical imaging system, which depicts the model of the heart M from the perspective of the viewer B on a CCD sensor 32. The CCD sensor 32 is connected to the display interface 33, and converts an image depicted on it into visual data VD and transmits the visual data VD via the display interface 33 to the presentation apparatus 10. The visual data VD can also be used simultaneously as model data MD and accordingly also transmitted to the model acquisition interface 23. The display data AD are transmitted via the display interface 33 to a display 34, which converts and displays the display data AD as an image. The image of the model of the heart M augmented with AR elements is mapped onto a projection surface 36 by an optical system 35 and made visible there for visual perception W by the viewer B.

Figure 3:
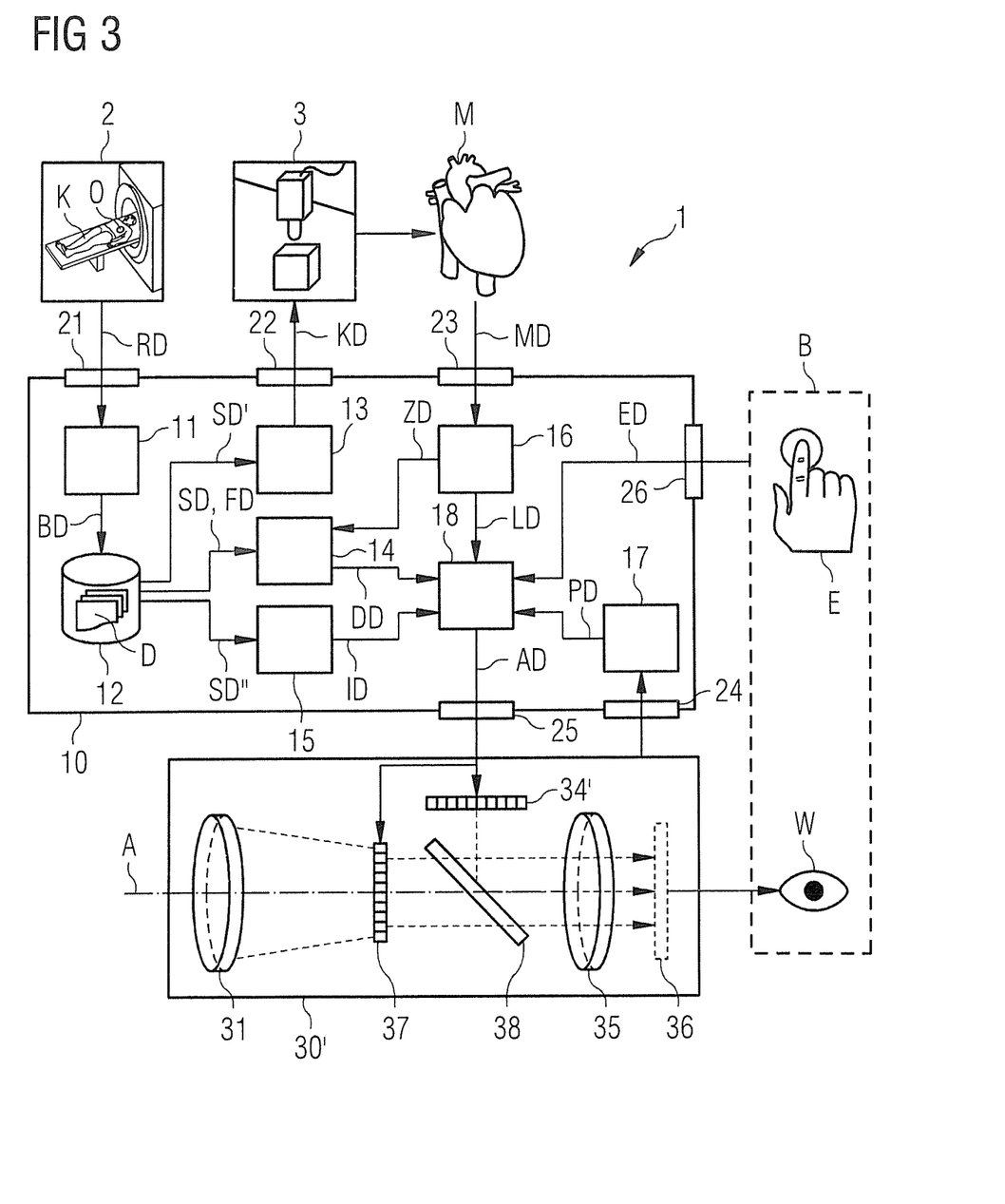
FIG. 3 shows a representation system similar to that in FIG. 2, but with an alternative embodiment of the AR display device.

FIG. 3 shows a representation system 1 similar to that in FIG. 2, but with an alternative embodiment of the AR headset 30'. The other components of the representation system 1, in particular the presentation apparatus 10, remain unchanged. In the case of the modified AR headset 30', a selective pixel-by-pixel shutter 37 on an optical axis A of the AR headset 30' is introduced behind the lens 31. Based on the display data AD, the shutter 37 masks image areas that are to be replaced by AR elements by becoming opaque in these areas. At a 45° angle to the optical axis A, a semi-opaque reflector 38 is arranged behind the shutter 37 on the optical axis A, seen from the model of the heart M. This lets the image with the masked areas through to the optical system 35 arranged on the optical axis A behind the semi-opaque reflector 38. Perpendicular to the optical axis A and at a 45° angle to the semi-opaque reflector, a display 34' is arranged such that an image shown thereon is projected from the semi-opaque reflector 38 onto the optical system 35. Based on the display data AD, the display 34' now augments precisely those areas of the model of the heart M selectively masked by the shutter 37 with AR elements, such that a complete image augmented by the AR elements is reproduced. This is mapped onto the projection surface 36 by the optical system 35 for visual perception W by the viewer B.

Figure 4:
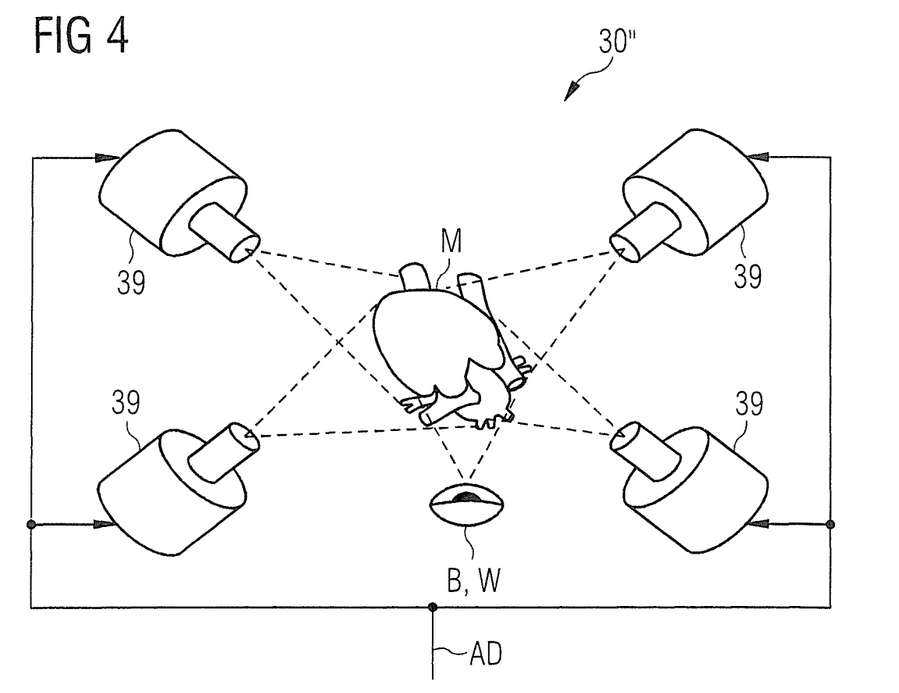
FIG. 4 is a schematic view of a further exemplary embodiment of an AR display device.

As an example, FIG. 4 schematically shows an alternative exemplary embodiment of an AR display device 30" with four projectors 39. The projectors 39 are arranged in relation to each other in a space such that they have defined directions of projection with a shared projection center. The model of the heart M onto which AR elements are projected from the projectors 39 is in the projection center. The projectors 39 are arranged such that the combined, shared projection in accordance with the display data AD which is transmitted by a display apparatus 10 according to the invention (not shown here) takes place onto all the surfaces of the model of the heart M. The model of the heart M and the displayed AR elements thus can be manipulated advantageously by one or more viewers B and detected by visual perception W. As aforementioned, the position and orientation of the model of the heart M in the space is recorded as model data MD, for example, by suitable cameras and position data LD derived therefrom. Using the position data LD, the projected image of the projectors 39 in their projection area is adjusted to the position and orientation of the model of the heart M. If necessary, the projectors 39 are also motor-aligned accordingly so that they track the position of the model of the heart M with their projection area.

The apparatuses and method described in detail herein are only exemplary embodiments, which can be modified by those skilled in the art in a wide variety of ways without departing from the inventive concept. In particular, not only image data of the heart, but also of other internal organs such as the brain, liver, bones and the like, as well as other image data of inorganic object such as valves in pipelines, etc. can serve as a basis for the method according to the invention. With an object model produced once according to the invention, for example, the steps of recording and display can naturally be executed repeatedly in the context of the invention. The term "element" does not preclude the component concerned from being composed of several interacting subcomponents which can, if necessary, also be distributed spatially.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for multisensory representation of an anatomical object of an individual patient, said method comprising:
   operating a medical imaging scanner according to a medical imaging procedure to obtain functional and/or dynamic data of an anatomical object of an individual patient to generate three-dimensional image data of the anatomical object;
   providing said three-dimensional image data to a processor and, in said processor, using said three-dimensional image data of the anatomical object of the individual patient to generate multidimensional digital model data of the anatomical object of the individual patient;

from said processor, operating an actual model fabricator, selected from the group consisting of a 3D printer and a CNC machine, in order to produce an actual three-dimensional model of said anatomical object of said individual patient;

detecting a position of said actual three-dimensional model of said anatomical object of said individual patient; and providing said multidimensional digital model data of the anatomical object of the individual patient, and an electronic signal representing said position of the actual three-dimensional model, to an augmented reality (AR) display device, and displaying, at said AR display device, at least a part of said multidimensional digital model of the anatomical object as a virtual augmentation of said functional and/or dynamic data, dependent on said position of the actual three-dimensional model of anatomical object of said individual patient, wherein said virtual augmentation of said functional and/or dynamic data is superimposed on said actual three-dimensional model of said anatomical object.

2. A method as claimed in claim 1 comprising generating said multidimensional digital model data in said processor by executing a CAD program in said processor.

3. A method as claimed in claim 1 comprising applying markers to said actual three-dimensional anatomical object of the individual patient, and detecting the position of the actual three-dimensional model of the anatomical object of the individual patient using said markers.

4. A method as claimed in claim 3 comprising selecting said markers from the group consisting of optical markers and RFID markers.

5. A method as claimed in claim 1 comprising also identifying, in said processor, a status of said actual three-dimensional model of said anatomical object of said individual patient, and displaying a said part of said multidimensional digital model data at said AR display device additionally dependent on said status.

6. A method as claimed in claim 1 comprising displaying said part of said multidimensional digital model data at said AR display device using a plurality of projectors.

7. A method as claimed in claim 1 comprising, said AR device, representing haptic properties of said actual three-dimensional model of said anatomical object of said individual patient, corresponding to haptic properties of said anatomical object of said individual patient.

8. A method as claimed in claim 1 wherein said functional and/or dynamic data represents non-visible functions and/or non-visible properties of the anatomical object.

9. A method as claimed in claim 8 wherein said non-visible functions and/or properties comprise at least one of: a fluid flow, a gas flow, a temperature, and a spatial temperature distribution.

10. A method as claimed in claim 1 wherein said superimposed virtual augmentation of said functional and/or dynamic data is at least partially transparent.

11. A method as claimed in claim 1 wherein said superimposed virtual augmentation of said functional and/or dynamic data is opaque.

12. A method as claimed in claim 1 wherein said functional and/or dynamic data represents non-structural aspects of the anatomical object.

13. A method as claimed in claim 1 wherein said functional and/or dynamic data represents non-visible, non-structural aspects of the anatomical object.

14. A representation system for multisensory representation of an anatomical object of an individual patient, said representation system comprising:

a medical imaging scanner operated according to a medical imaging procedure to obtain functional and/or dynamic data of an anatomical object of an individual patient to generate three-dimensional image data of the anatomical object;

a processor provided with said three-dimensional image data, said processor being configured to use said three-dimensional image data of the anatomical object of the individual patient to generate multidimensional digital model data of the anatomical object of the individual patient;

an actual model fabricator, selected from the group consisting of a 3D printer and a CNC machine, operated by said processor in order to produce an actual three-dimensional model of said anatomical object of said individual patient;

a detector that detects a position of said actual three-dimensional model of said anatomical object of said individual patient; and an augmented reality (AR) display device provided with said multidimensional digital model data of the anatomical object of the individual patient, and an electronic signal representing said position of the actual three-dimensional model, said AR display device displaying a part of said multidimensional digital model of the anatomical object as a virtual augmentation of said functional and/or dynamic data, dependent on said position of the actual three-dimensional model of anatomical object of said individual patient, wherein said virtual augmentation of said functional and/or dynamic data is superimposed on said actual three-dimensional model of said anatomical object.

* * * * *